(12) United States Patent
Matta et al.

(10) Patent No.: US 9,693,675 B2
(45) Date of Patent: Jul. 4, 2017

(54) CLEANING COMPOSITION

(71) Applicant: Medivators Inc., Minneapolis, MN (US)

(72) Inventors: John J. Matta, Shoreview, MN (US); Tuan Nguyen, Chaska, MN (US); Huyen Phuong Bui, Brooklyn Park, MN (US)

(73) Assignee: Medivators Inc., Minneapolis, MN (US)

( * ) Notice: Subject to any disclaimer, the term of this patent is extended or adjusted under 35 U.S.C. 154(b) by 146 days.

(21) Appl. No.: 14/578,381

(22) Filed: Dec. 20, 2014

(65) Prior Publication Data

US 2016/0175051 A1    Jun. 23, 2016

(51) Int. Cl.
- *B08B 9/00* (2006.01)
- *A61B 1/005* (2006.01)
- *A61B 1/12* (2006.01)
- *A61B 19/00* (2006.01)
- *B08B 9/02* (2006.01)
- *C11D 1/72* (2006.01)
- *C11D 3/00* (2006.01)
- *C11D 3/20* (2006.01)
- *C11D 3/33* (2006.01)
- *C11D 11/00* (2006.01)
- *C11D 7/06* (2006.01)
- *C11D 7/16* (2006.01)
- *C11D 7/26* (2006.01)
- *C11D 7/32* (2006.01)

(52) U.S. Cl.
CPC ............. *A61B 1/005* (2013.01); *A61B 1/123* (2013.01); *A61B 19/34* (2013.01); *B08B 9/02* (2013.01); *C11D 1/72* (2013.01); *C11D 3/0047* (2013.01); *C11D 3/2048* (2013.01); *C11D 3/33* (2013.01); *C11D 7/06* (2013.01); *C11D 7/16* (2013.01); *C11D 7/261* (2013.01); *C11D 7/263* (2013.01); *C11D 7/3245* (2013.01); *C11D 11/0023* (2013.01); *C11D 11/0041* (2013.01); *A61B 2019/343* (2013.01)

(58) Field of Classification Search
CPC ........ C23G 1/02; C09D 9/00; C11D 11/0041; C11D 3/0052; B08B 9/032; F28G 9/00; C02F 5/12

USPC ............... 134/3, 4, 22.14, 22.13, 22.19, 41; 252/79, 79.41
See application file for complete search history.

(56) References Cited

U.S. PATENT DOCUMENTS

| | | | | |
|---|---|---|---|---|
| 4,357,254 A | * | 11/1982 | Kapiloff ................. | B01D 61/10 134/42 |
| 5,772,876 A | * | 6/1998 | Murakami ............. | B01J 20/286 210/198.2 |
| 5,972,876 A | * | 10/1999 | Robbins ............. | C11D 17/0043 134/40 |
| 7,670,549 B2 | * | 3/2010 | Geret ........................ | B08B 3/08 134/22.19 |
| 2013/0296213 A1 | | 11/2013 | Isobe et al. | |
| 2015/0361377 A1 | * | 12/2015 | Kron ...................... | C11D 1/004 510/238 |

FOREIGN PATENT DOCUMENTS

| | | |
|---|---|---|
| EP | 1327674 A1 | 7/2003 |
| WO | WO-2012045365 A1 | 4/2012 |

OTHER PUBLICATIONS

"International Application Serial No. PCT/US2015/066686, International Search Report mailed Apr. 21, 2016", 5 pgs.

"International Application Serial No. PCT/US2015/066686, Written Opinion mailed Apr. 21, 2016", 6 pgs.

"International Application Serial No. PCT/US2015/066686, Response filed Oct. 11, 2016 to Written Opinion mailed Apr. 21, 2016", 17 pgs.

* cited by examiner

*Primary Examiner* — Duy Deo
*Assistant Examiner* — Maki Angadi
(74) *Attorney, Agent, or Firm* — Schwegman Lundberg & Woessner, P.A.

(57) ABSTRACT

Provided herein is a composition that includes: (i) chelator (e.g., ethylenediaminetetraacetic acid (EDTA)), (ii) buffer system (e.g., potassium phosphate dibasic and sodium hydroxide), (iii) cleaner (e.g., diethyl glycol monoethyl ether), (iv) solubilizer (e.g., propylene glycol), and (v) diluent (e.g., water), wherein the composition has a pH of at least about 9.5. Also provided is a method of cleaning a medical device that includes contacting the medical device with the composition described herein, for a period of time effective to clean the medical device. Subsequent to the cleaning, the medical device can optionally be disinfected, dried, and stored.

2 Claims, No Drawings

CLEANING COMPOSITION

BACKGROUND OF THE INVENTION

The medical industry and other industries utilize devices that are required to be cleaned and decontaminated. Cleaning includes the removal of foreign material, including organic soil such as blood, feces, respiratory secretions, etc., from a substrate. It has been reported that failure to remove foreign material from a medical device such as an endoscope before a disinfection or sterilization process is likely to render the process ineffective. (Rutala, W A, APIC Guideline for Selection and Use of Disinfectants, Am J Infect Control, August 1996; Vol. 24, 4:313-342). The presence of organic material or soil may contribute to the failure of disinfection by harboring embedded microbes and preventing the penetration of the germicide. Additionally, some disinfectants are inactivated by organic material (Martin, M A, Reichelderfer, M, APIC Guideline for Infection Prevention and Control in Flexible Endoscopy, Am J Infect Control, 1994; 22:19-38). Thus, there exists a need for a safe, practical, and efficient cleaning compositions and method for reprocessing medical devices.

SUMMARY OF THE INVENTION

The present invention provides a composition that includes: (i) chelator, (ii) buffer system, (iii) cleaner, (iv) solubilizer, and (v) diluent, wherein the composition has a pH of at least about 9.5.

The present invention also provides a composition that includes: (i) chelator that includes ethylenediaminetetraacetic acid (EDTA), present in about 0.5 to about 2.0 wt. % of the composition; (ii) buffer system that includes potassium phosphate dibasic and sodium hydroxide, present in a total amount of about 10 to about 20 wt. % of the composition; (iii) cleaner that includes diethyl glycol monoethyl ether, present in about 2.5 to about 10 wt. % of the composition; (iv) solubilizer that includes propylene glycol, present in about 5 to about 15 wt. % of the composition; and (v) diluent that includes water, present in about 60 to about 70 wt. % of the composition; wherein the composition has a pH of at least about 9.5.

The present invention also provides a composition that includes: (i) chelator that includes ethylenediaminetetraacetic acid (EDTA), present in about 1.0 wt. % of the composition; (ii) buffer system that includes potassium phosphate dibasic and sodium hydroxide, present in about 14.2 wt. % and 2.16 wt. %, respectively, of the composition; (iii) cleaner that includes diethyl glycol monoethyl ether, present in about 5.0 wt. % of the composition; (iv) solubilizer that includes propylene glycol, present in about 10.0 wt. % of the composition; and (v) diluent that includes water, present in about 67.64 wt. % of the composition; wherein the composition has a pH of about 11.9 to about 12.2.

The present invention also provides a composition that includes: (i) chelator that includes ethylenediaminetetraacetic acid (EDTA), present in about 1.0 wt. % of the composition; (ii) buffer system that includes potassium phosphate dibasic and sodium hydroxide, present in about 14.200 wt. % and 2.160 wt. %, respectively, of the composition; (iii) cleaner that includes diethyl glycol monoethyl ether, present in about 5.0 wt. % of the composition; (iv) solubilizer that includes propylene glycol, present in about 10.0 wt. % of the composition; and (v) diluent that includes water, present in about 68.617 wt. % of the composition; wherein the composition has a pH of about 9.5 to about 11.5.

The present invention also provides a composition that includes a method of cleaning a medical device, the method includes contacting the medical device with the composition described herein for a period of time effective to clean the medical device. Subsequent to the cleaning, the medical device can optionally be disinfected, dried and stored.

DETAILED DESCRIPTION OF THE INVENTION

Reference will now be made in detail to certain claims of the present invention, examples of which are illustrated in the accompanying structures and formulas. While the present invention will be described in conjunction with the enumerated claims, it will be understood that the present invention is not intended to limit those claims. On the contrary, the present invention is intended to cover all alternatives, modifications, and equivalents, which can be included within the scope of the present invention, as defined by the claims.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" should be interpreted to include not only the explicitly recited amount of about 0.1 wt. % to about 5 wt. %, but also the individual concentrations (e.g., 1%, 2%, 3%, and 4%) and the sub-ranges (e.g., 0.5%, 1.1%, 2.2%, 3.3%, and 4.4%) within the indicated range.

The present invention relates to cleaning compositions, methods of using the cleaning compositions, and/or kits that include the cleaning compositions. In specific embodiments, the composition includes: (i) chelator, (ii) buffer system, (iii) cleaner, (iv) solubilizer, and (v) diluent, wherein the composition has a pH of at least about 9.5.

When describing the present invention, the following terms have the following meanings, unless otherwise indicated.

The term "about" can allow for a degree of variability in a value or range, for example, within 10%, within 5%, or within 1% of a stated value or of a stated limit of a range.

As used herein, "chelator" refers to a compound capable of forming two or more separate coordinate bonds between a polydentate (multiple bonded) ligand and a single central atom. Usually these ligands are organic compounds, and are called chelants, chelators, chelating agents, or sequestering agents. In specific embodiments of the invention, the chelator can include ethylenediaminetetraacetic acid (EDTA).

As used herein, "buffer system" refers to a mixture of a weak acid and its conjugate base, or vice versa. Its pH changes very little when a small amount of strong acid or base is added to it and thus it is used to prevent changes in the pH of a solution. Buffer solutions are used as a means of keeping pH at a nearly constant value in a wide variety of chemical applications. In specific embodiments of the invention, the buffer system can include potassium phosphate dibasic and sodium hydroxide.

As used herein, "cleaner" refers to a substance capable of effectively cleaning a substrate (e.g., medical device). The substance can effectively remove foreign or extraneous matter from the substrate. In specific embodiments of the invention, the cleaner can include diethyl glycol monoethyl ether.

As used herein, "solubilizer" refers to a substance that makes soluble, aids in the solubility, or otherwise increases the solubility, of a substance in a liquid diluent or carrier. In specific embodiments of the invention, the solubilizer can include propylene glycol.

As used herein, "diluent" or "carrier" refers to a liquid medium in which substances are suspended, completely dissolved, or partially dissolved in. In specific embodiments of the invention, the diluent can include water (e.g., DI water).

As used herein, "pH" refers to the measure of the acidity or basicity of an aqueous solution. Solutions with a pH less than 7 are said to be acidic and solutions with a pH greater than 7 are basic or alkaline. Pure water has a pH very close to 7. The pH scale is traceable to a set of standard solutions whose pH is established by international agreement. Primary pH standard values are determined using a concentration cell with transference, by measuring the potential difference between a hydrogen electrode and a standard electrode such as the silver chloride electrode. Measurement of pH for aqueous solutions can be done, e.g., with a glass electrode and a pH meter, or using indicators. Mathematically, pH is the negative logarithm of the activity of the (solvated) hydronium ion, more often expressed as the measure of the hydronium ion concentration.

In specific embodiments, the pH of the concentrate can be about 11.9 to 12.2. Upon dilution with a suitable amount of diluent (e.g., at a 0.5% concentration of concentrate), the pH of the resulting solution can be about 9.5 to about 11.5. It is appreciated that those of skill in the art understand that when water is used as the diluent, the pH of a solution may be affected by the type of water used: deionized water, reversed osmosis water, or tap water (which can vary from region to region). This contributes to the range of pH values (e.g., about 9.5 to about 11.5) upon dilution to a 0.5% concentration of concentrate, as the pH of the solution may be affected by the type of water used (e.g., fresh water or purified water).

As used herein, "purified water" refers to water that is mechanically filtered or processed to be cleaned for consumption. Distilled water and deionized (DI) water have been the most common forms of purified water, but water can also be purified by other processes including reverse osmosis, carbon filtration, microfiltration, ultrafiltration, ultraviolet oxidation, or electrodialysis.

As used herein, "deionized water" or "DI water" refers to demineralized water/DM water (DI water, DIW or de-ionized water), which is water that has had almost all of its mineral ions removed, such as cations like sodium, calcium, iron, and copper, and anions such as chloride and sulfate. Deionization is a chemical process that uses specially manufactured ion-exchange resins which exchange hydrogen ion and hydroxide ion for dissolved minerals, which then recombine to form water. Because most non-particulate water impurities are dissolved salts, deionization produces a high purity water that is generally similar to distilled water, and this process is quick and without scale buildup. However, deionization does not significantly remove uncharged organic molecules, viruses or bacteria, except by incidental trapping in the resin. Specially made strong base anion resins can remove Gram-negative bacteria. Deionization can be done continuously and inexpensively using electrodeionization.

As used herein, "reversed osmosis water" refers to purified water obtained using a semipermeable membrane. This membrane technology is not properly a filtration method. In reverse osmosis, an applied pressure is used to overcome osmotic pressure, a colligative property, that is driven by chemical potential, a thermodynamic parameter. Reverse osmosis can remove many types of molecules and ions from solutions, and is used in both industrial processes and the production of potable water. The result is that the solute is retained on the pressurized side of the membrane and the pure solvent is allowed to pass to the other side. To be "selective," this membrane should not allow large molecules or ions through the pores (holes), but should allow smaller components of the solution (such as the solvent) to pass freely As used herein, "tap water" or "running water," "city water," or "municipal water" refers to water supplied to a tap (valve). Its uses include drinking, washing, cooking, and the flushing of toilets. Indoor tap water is distributed through "indoor plumbing", which has existed since antiquity but was available to very few people until the second half of the 19th century, when it began to propagate in what are now the developed countries. It became common in many regions during the 20th century, and is now lacking only among the poor, especially in developing countries. Calling a water supply "tap water" distinguishes it from the other main types of fresh water which may be available; these include water from rainwater-collecting cisterns, water from village pumps or town pumps, or water carried from streams, rivers, or lakes (whose potability may vary).

As used herein, "medical device" refers to an instrument, apparatus, implant, in vitro reagent, or similar or related article that is used to diagnose, prevent, or treat disease or other conditions, and does not achieve its purposes through chemical action within or on the body (which would make it a drug). Whereas medicinal products (also called pharmaceuticals) achieve their principal action by pharmacological, metabolic or immunological means, medical devices act by other means like physical, mechanical, or thermal means. Medical devices vary greatly in complexity and application. Examples range from simple devices such as tongue depressors, medical thermometers, and disposable gloves to advanced devices such as computers which assist in the conduct of medical testing, implants, and prostheses. The design of medical devices constitutes a major segment of the field of biomedical engineering. In specific embodiments, the medical device can include an endoscope (e.g., flexible endoscope).

As used herein, "endoscope" refers to an instrument used to examine the interior of a hollow organ or cavity of the body. Unlike most other medical imaging devices, endoscopes are inserted directly into the organ. Endoscope can also refer to using a borescope in technical situations where direct line of-sight observation is not feasible.

An endoscope can consist of: (a) a rigid or flexible tube; (b) a light delivery system to illuminate the organ or object under inspection. The light source is normally outside the body and the light is typically directed via an optical fiber system; (c) a lens system transmitting the image from the objective lens to the viewer, typically a relay lens system in the case of rigid endoscopes or a bundle of fiberoptics in the case of a fiberscope; (d) an eyepiece. Modern instruments may be videoscopes, with no eyepiece, a camera transmits image to a screen for image capture; and (e) an additional channel to allow entry of medical instruments or manipulators.

As used herein, "flexible endoscope" refers to an endoscope that includes a flexible tube.

As used herein, "flexible endoscope washer disinfector device" or "washer disinfector device" refers to an apparatus or machine employed to wash a medical device, such as a flexible endoscope or colonoscope. Such an apparatus or machine can also disinfect the medical device, as well as optionally dry and optionally store the medical device. Suitable apparatus or machines that can wash and disinfect the medical device include, e.g., a WASSENBURG® PAA Cleaner; WASSENBURG® WD440 Endoscope Washer Disinfector; and WASSENBURG® WD440 PT Pass Through Endoscope Washer Disinfector. Suitable apparatus or machines that can dry and store the medical device include, e.g., a WASSENBURG® DRY300 Drying and Condition Cabinet; and WASSENBURG® DRY200 Endoscope Drying and Conditioning Cabinet.

As used herein, "clean," "cleaning," "wash," or "washing" refers to the process of freeing a substrate from foreign or extraneous matter; the process of removing foreign or extraneous matter from a substrate (e.g., medical device).

As used herein, "disinfect" or "disinfecting" refers to the process of destroying, removing, killing and/or inhibiting the action of microorganisms located on a substrate (e.g., medical device).

As used herein, "dry" or "drying" refers to the process of removing moisture from a substrate (e.g., medical device). The process can be carried out, e.g., employing heat (elevated temperature).

As used herein, "store" or "storing" refers to the process of housing a substrate (e.g., medical device) for future use.

As used herein, the term "EndoHigh®Disinfectant" refers to a disinfecting composition that includes about 20.0 to about 26.0 wt. % hydrogen peroxide, about 9.0 to about 11.0 wt. % acetic acid, about 1.0 wt. % Dequest® 2010, about 2.0 wt. % Pluronic® 10R5 surfactant block copolymer, about 53 wt. % deionized water and about 6.8 to about 7.5 wt. % peracetic acid.

As used herein, the term "Dequest® 2010" refers to the compound (1-hydroxyethylidene-1,1,-diphosphonic acid, or 1-hydroxyethane 1,1-diphosphonic acid, or HEDP. It has a CAS Reg. No. of 2809-21-4.

As used herein, the term "Pluronic® 10R5 surfactant block copolymer" refers to Polyoxypropylene-polyoxyethylene block copolymer, having the CAS Reg. No. 9003-11-6.

As used herein, term "EndoHigh®Cleaner" refers to a cleaning composition of the present invention that includes: (i) chelator that includes ethylenediaminetetraacetic acid (EDTA), present in about 1.0 wt. % of the composition; (ii) buffer system that includes potassium phosphate dibasic and sodium hydroxide, present in about 14.2 wt. % and 2.16 wt. %, respectively, of the composition; (iii) cleaner that includes diethyl glycol monoethyl ether, present in about 5.0 wt. % of the composition; (iv) solubilizer that includes propylene glycol, present in about 10.0 wt. % of the composition; and (v) diluent that includes water, present in about 67.64 wt. % of the composition; wherein the composition has a pH of about 11.9 to about 12.2.

In specific embodiments, the composition of the present invention can be formulated as, can exist as, and can be commercially available as a liquid concentrate cleaning composition. The term "liquid concentrate" refers to a composition that is relatively undiluted and concentrated, having a low content of carrier or diluent, e.g., water. Having the composition be commercially available as a liquid concentrate will typically save costs associated with the manufacturing, shipping, and/or storage of the product.

When the composition of the present invention is formulated as a liquid concentrate, the concentrate can subsequently be diluted with an appropriate amount of carrier or diluent (e.g., water), prior to use. Additionally, although considered to be a concentrate, when the composition of the present invention is formulated as a liquid concentrate, a discrete and finite amount of carrier or diluent (e.g., water) can be employed.

The term "cleaning composition" refers to a substance that when applied to non-living objects, effectively removes foreign matter located on the objects. For example, when used to clean medical devices, such as flexible endoscopes, the cleaning composition of the present invention can effectively remove from the medical device at least one of soil, blood, protein, carbohydrate, bodily fluid, and fecal matter.

In specific embodiments, the composition of the present invention can be relatively non-corrosive. The term "non-corrosive" or "noncorrosive" refers to a substance that will not destroy or irreversibly damage another surface or substance with which it comes into contact. The main hazards to people include damage to the eyes, the skin, and the tissue under the skin; inhalation or ingestion of a corrosive substance can damage the respiratory and gastrointestinal tracts. Exposure results in chemical burn. Having the composition be relatively non-corrosive will allow the user to employ the composition over a wider range of uses, exposing the composition to a wider range of substrates. For example, having the composition be relatively non-corrosive will allow the user to employ the composition as a cleaner with certain medical devices that are highly sensitive to corrosive substances.

In specific embodiments, the composition of the present invention can be relatively non-toxic. The term "non-toxic" refers to a substance that has a relatively low degree to which it can damage a living or non-living organism. Toxicity can refer to the effect on a whole organism, such as an animal, bacterium, or plant, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom there is a dose below which there is no detectable toxic effect. Having the composition be relatively non-toxic will allow a wider range of users be able to safely handle the composition, without serious safety concerns or risks.

In specific embodiments, the composition of the present invention can be stable over extended periods of time (i.e., has a long-term stability). The term "long-term stability" refers to a substance undergoing little or no physical and/or chemical decomposition or degradation, over extended periods of time.

In further specific embodiments, the composition of the present invention can be stable over extended periods of time, such that at about 1 atm and about 19° C., less than about 5 wt. % of each component independently degrades over about one year. In additional specific embodiments, the composition of the present invention can be stable over extended periods of time, such that at about 1 atm and about 19° C., at least about 95 wt. % of each component is independently present after about one year.

Having the composition be relatively stable over extended periods of time will allow the composition to retain its effectiveness over that time, ensuring that it will remain useful and active for its intended purpose. In contrast, in those compositions that do not retain their effectiveness over that time, product loss can result, which can be financially costly. Additionally, risks associated with the use of a product that has lost some or all of its effectiveness for the intended purpose can be hazardous, in that the product may not effectively achieve the desired goal. For example, when used to clean a medical device, use of a composition that has lost some or all of its effectiveness as a cleaning composition may not effectively clean the medical device. Medical injuries can be sustained by the patient, including serious infections.

In specific embodiments, the composition of the present invention can be formulated as, can exist as, and is commercially available as, a one-part composition. The term "one-part composition" refers to all chemical components of a composition being present together, such that they are each in intimate and physical contact with one another, and are each present in a single container. Having the composition be commercially available as a one-part composition will be more cost effective (e.g., lower manufacturing costs associated with fewer containers), and will avoid the necessity of the user mixing or combining multiple components together, prior to using.

The present invention also provides for a kit that includes: (a) an enclosed container that includes a removable closure; (b) the composition of the present invention as described herein, which is located inside the enclosed container; and (c) printed indicia located on the enclosed container.

In specific embodiments, the enclosed container can be opaque. In additional specific embodiments, the enclosed container can be manufactured from high density polyethylene (HDPE), thereby providing the requisite opacity. Having the enclosed container be manufactured from high density polyethylene (HDPE) will decrease the likelihood that the composition will degrade and/or decompose over extended periods of time, due to excessive exposure to direct sunlight.

The term "high-density polyethylene" or "HDPE" refers to a polyethylene thermoplastic made from petroleum. The mass density of high-density polyethylene can range from 0.93 to 0.97 g/cm$^3$. Although the density of HDPE is only marginally higher than that of low-density polyethylene, HDPE has little branching, giving it stronger intermolecular forces and tensile strength than LDPE. The difference in strength exceeds the difference in density, giving HDPE a higher specific strength. It is also harder and more opaque and can withstand somewhat higher temperatures (120° C./248° F. for short periods, 110° C./230° F. continuously). HDPE is resistant to many different solvents.

The term "opaque" refers to an object that is neither transparent (allowing all light to pass through) nor translucent (allowing some light to pass through). When light strikes an interface between two substances, in general some may be reflected, some absorbed, some scattered, and the rest transmitted (also see refraction). Reflection can be diffuse, for example light reflecting off a white wall, or specular, for example light reflecting off a mirror. An opaque substance transmits no light, and therefore reflects, scatters, or absorbs all of it. Both mirrors and carbon black are opaque. Opacity depends on the frequency of the light being considered. For instance, some kinds of glass, while transparent in the visual range, are largely opaque to ultraviolet light. More extreme frequency-dependence is visible in the absorption lines of cold gases.

To further decrease the likelihood that the composition will degrade and/or decompose over extended periods of time, the composition should avoid, when feasible: excessive exposure to direct sunlight, excessive heat and/or elevated temperatures. As such, in specific embodiments, the enclosed container of the kit can include printed indicia, with instructions to avoid excessive heat, elevated temperatures, direct sunlight, or a combination thereof.

In specific embodiments, the composition can effectively clean a substrate. In further specific embodiments, the composition can effectively clean the surface of a substrate.

The composition of the present invention can be formulated for application, depending upon the user's preference as well as the ultimate application of the composition. For example, the composition can be formulated for use in a sprayable composition, atomized liquid sprayer, or liquid applicator. Such formulations can include at least one of a spray bottle, motorized sprayer, wipe, cloth, sponge, non-woven fabric, and woven fabric. Such formulations may be particularly suitable for applying the composition to a surface of a hospital, physician's office, medical clinic, medical facility, dental office, dental facility, airport, school, pet store, zoo, children's day care, elderly nursing home, museum, movie theatre, athletic facility, sporting arena, gymnasium, rest room, bathroom, shopping center, amusement park, church, synagogue, mosque, temple, restaurant, food processing facility, food manufacturing facility, pharmaceutical company, hot-tub, sauna, and/or clean room.

Such liquid formulations may be particularly suitable for applying the composition to metal, plastic, natural rubber, polysilicone, synthetic rubber, glass, stone, grout, fiberglass, wood, concrete, construction products, and/or building products.

In specific embodiments, the composition of the invention can be configured for use in contacting at least one of medical equipment, medical device (e.g., reusable medical device or instrument, such as a colonoscope or endoscope), surface in the medical industry, dental equipment, dental device, and surface in the dental industry. In a further specific embodiment, the composition of the invention can be configured for use in contacting a medical device (e.g., reusable medical device or instrument). In particular, the composition of the invention may be used in the reconditioning of a soiled endoscope. In this reconditioning method, the compositions of the invention are useful during the cleaning process following use of the endoscope in a medical procedure.

The invention will now be described by the following non-limiting examples.

Example 1

Preparation of the Endoscopes

Endoscopes were used for standard clinical exams. They were then manually cleaned by the clinic's standard procedure with no extraordinary soil removal.

Exposure to Test Substance

On a WASSENBURG® WD440 the parameters were adjusted to a 5 minute disinfection cycle with a running temperature of 35±2° C. EndoHigh®Disinfectant and a disinfectant of the present invention (e.g., EndoHigh® Cleaner) in bottles were connected to the system. The detergent reservoir was filled with a disinfectant of the present invention (e.g., EndoHigh® Cleaner). The manually cleaned clinical endoscope was inserted into the WD440 and a full cycle was completed. After the full cycle, the lid was opened and the adapters and endoscope were aseptically removed from the machine. The endoscope was aseptically placed in a sterile bin. 150-175 ml of neutralizer (e.g., peptone, sodium thiosulfate, and potassium phosphate and 0.1% tween) was injected into the adapter base to stop the action of residual disinfectant in the endoscope channels. Liquid was collected from the distal tip into a sterile wide-mouth bottle.

Recovery of Surviving Organisms

The method for eluting the test system from the test article was derived from procedures described by Bond and Hedrick. See W. W. Bond and E. R. Hedrick, 1992. Microbiological Culturing of Environmental and Medical Device Surfaces. In H. D. Isenberg and M. J. R. Gilchrist (eds.), Clinical Microbiological Procedures Handbook, Section 11: Epidemiologic and Infection Control Microbiology, American Society for Microbiology, Washington, D.C., pgs. 11.10.1-11.10.9.

External: 100 ml of neutralizer was dispensed into a sterile wide mouth bottle. Two sterile gauze sponges were moistened with 10 ml of neutralizer. Wearing sterile gloves, the excess neutralizer fluid was squeezed from the sponge and the exterior of the insertion tube was wiped, using 3 back-and-forth strokes across the portion. The sponge was placed into the bottle containing 100 ml of neutralizer. Wiping was repeated with second sponge.

Internal: The distal end of the endoscope was placed in a sterile wide mouth bottle. The biopsy channel was flushed with 100 ml of neutralizer and ≥100 ml of air using a sterile syringe. The air/water channel was flushed with approximately 20 ml neutralizer, followed by approximately 20 ml of air, approximately 10 ml of neutralizer, and approximately 20 ml of air. The auxiliary water channel was flushed with approximately 10 ml neutralizer, approximately 10 ml of air, and approximately 5 ml neutralizer, approximately 10 ml of air. The biopsy channel was brushed with a sterile brush from the control head to the distal tip 5 times. As the brush emerged from the distal tip, the brush tip was ensured to be submerged in the neutralizer to remove any additional adherent organisms. The biopsy channel was then flushed with 45-55 ml of neutralizer and ≥50 ml of air.

The bottles containing the sponges were sonicated for 5 minutes, then swirled for one minute. The contents of all bottles were filtered through 0.22 μm filter and rinsed with two 25-30 ml portions of sterile saline solution. Each filter was placed on TSA and incubated for 37±2° C. for ≥3 days.

The environment during recovery was monitored by using appropriately placed TSA plates and incubated for 37±2° C. for ≥21 days.

Controls

Neutralizer validation: (1) 1.0 ml of disinfectant was added to 50 ml of neutralizer and mixed. (2) At 5 minutes, 1.0 ml of 1-3×10$^2$ CFU/ml cell suspension was added to the neutralizer mix. (3) After 30 minutes, the entire contents were filtered and filters were each placed on TSA. The plates were incubated at 37±2° C. for ≥3 days. Neutralizer toxicity: (1) 1.0 of 1-3×102 CFU/ml cell suspension was added to 50 ml of neutralizer. (2) After 30 minutes, the entire contents were filtered and each filter was placed on TSA. The plates were incubated at 37±2° C. for ≥3 days.

Results

The following results were obtained:

TABLE 1

Results of clinically used colonoscopes washed and disinfected by the Wassenburg WD440 using (1) EndoHigh ®Disinfectant and (2) EndoHigh ®Cleaner at nominal conditions, 35° C.

| Trial # | Survivors |
|---|---|
| 1 | 0 |
| 2 | 0 |
| 3 | 0 |

TABLE 2

Controls were measured by performing a neutralizer validation to ensure that the disinfectant was effectively neutralized. The test organism used was Staphylococcus aureus. Each sample was inoculated with about 34 CFU. An average of 88.23% of organisms were recovered.

| Sample | CFU Recovered | Percent Recovery |
|---|---|---|
| A | 38 | 111.76 |
| B | 22 | 64.71 |

TABLE 3

Controls were measured by performing a neutralizer toxicity test to ensure that the neutralizer was not toxic to the test organism. The test organism used was Staphylococcus aureus. Each sample was inoculated with about 34 CFU. An average of 91.18% of organisms were recovered.

| Sample | CFU Recovered | Percent Recovery |
|---|---|---|
| A | 32 | 94.12 |
| B | 30 | 88.24 |

CONCLUSIONS

EndoHigh®PAA, EndoHigh®Cleaner, and WASSENBURG® WD440 were capable of washing and high level disinfecting clinically used colonoscopes that have been prewashed using the clinic's standard washing procedure. Further, this met the clinical evaluation report requirements per EU medical device guidance MEDDEV 2.7.1 by achieving the required zero survivors of organisms, and supporting a high level disinfection claim as described in the guidelines for submissions for endoscope washer/disinfectors.

Enumerated Embodiments

The following enumerated embodiments [1] to [43] are provided for further illustration and description. All combinations and sub-combinations embraced within the enumerated embodiments below are contemplated herein and form part of the present invention, as defined by the claims.

[1.] The present invention provides a composition that includes:
(i) chelator,
(ii) buffer system,
(iii) cleaner,
(iv) solubilizer, and
(v) diluent
the composition having a pH of at least about 9.5.

[2.] The composition of the above embodiment, wherein the chelator includes ethylenediaminetetraacetic acid (EDTA).

[3.] The composition of any one of the above embodiments, wherein the chelator is present in about 0.5 to about 2.0 wt. % of the composition.
[4.] The composition of any one of the above embodiments, wherein the chelator is present in about 1.0 wt. % of the composition.
[5.] The composition of any one of the above embodiments, wherein the buffer system includes potassium phosphate dibasic and sodium hydroxide.
[6.] The composition of any one of the above embodiments, wherein the buffer system comprises potassium dibasic monohydrate.
[7.] The composition of any one of the above embodiments, wherein the buffer system comprises sodium hydroxide.
[8.] The composition of any one of the above embodiments, wherein the buffer system comprises potassium dibasic monohydrate and sodium hydroxide.
[9.] The composition of any one of the above embodiments, wherein the buffer system is present in about 10 to about 25 wt. % of the composition.
[10.] The composition of any one of the above embodiments, wherein the buffer system is present in about 10 to about 20 wt. % of the composition.
[11.] The composition of any one of the above embodiments, wherein the cleaner includes diethyl glycol monoethyl ether.
[12.] The composition of any one of the above embodiments, wherein the cleaner is present in about 2.5 to about 10 wt. % of the composition.
[13.] The composition of any one of the above embodiments, wherein the solubilizer includes propylene glycol.
[14.] The composition of any one of the above embodiments, wherein the solubilizer is present in about 5 to about 15 wt. % of the composition.
[15.] The composition of any one of the above embodiments, wherein the diluent includes deionized (DI) water.
[16.] The composition of any one of the above embodiments, wherein the diluent is present in about 60 to about 70 wt. % of the composition.
[17.] The composition of any one of the above embodiments, which is a concentrate, having a pH of at least about 9.5.
[18.] The composition of any one of the above embodiments, which is a concentrate, having a pH of about 11.9 to about 12.2.
[19.] The composition of any one of the above embodiments, which is diluted to 0.5% concentration with at least one of purified water and fresh water, the diluted composition having a pH of about 9.5 to about 11.5.
[20.] The present invention also provides a composition that includes:
  (i) chelator including ethylenediaminetetraacetic acid (EDTA), present in about 0.5 to about 2.0 wt. % of the composition;
  (ii) buffer system including potassium phosphate dibasic and sodium hydroxide, present in a total amount of about 10 to about 20 wt. % of the composition;
  (iii) cleaner including diethyl glycol monoethyl ether, present in about 2.5 to about 10 wt. % of the composition;
  (iv) solubilizer including diethyl glycol monoethyl ether, present in about 2.5 to about 10 wt. % of the composition; and
  (v) diluent including water, present in about 60 to about 70 wt. % of the composition;
the composition having a pH of at least about 9.5.
[21.] The composition of embodiment [20], which is a concentrate, the composition having a pH of about 11.9 to about 12.2.

[22.] The present invention also provides a composition that includes:
  (i) chelator including ethylenediaminetetraacetic acid (EDTA), present in about 1.0 wt. % of the composition;
  (ii) buffer system including potassium phosphate dibasic and sodium hydroxide, present in about 14.2 wt. % and 2.16 wt. %, respectively, of the composition;
  (iii) cleaner including diethyl glycol monoethyl ether, present in about 5.0 wt. % of the composition;
  (iv) solubilizer including diethyl glycol monoethyl ether, present in about 10.0 wt. % of the composition; and
  (v) diluent including water, present in about 67.64 wt. % of the composition; the composition having a pH of about 11.9 to about 12.2.
[23.] The composition of embodiment [20] or [22], which is diluted to 0.5% concentration with at least one of purified water and fresh water; the diluted composition having a pH of about 9.5 to about 11.5.
[24.] The present invention also provides a composition that includes:
  (i) chelator including ethylenediaminetetraacetic acid (EDTA), present in about 1.0 wt. % of the composition;
  (ii) buffer system including potassium phosphate dibasic and sodium hydroxide, present in about 14.200 wt. % and 2.160 wt. %, respectively, of the composition;
  (iii) cleaner including diethyl glycol monoethyl ether, present in about 5.0 wt. % of the composition;
  (iv) solubilizer including propylene glycol, present in about 10.0 wt. % of the composition; and
  (v) diluent including water, present in about 67.64 wt. % of the composition; the composition having a pH of about 11.9 to about 12.2.
[25.] The present invention also provides a method of cleaning a medical device, the method includes contacting the medical device with the composition of any one of the embodiments for a period of time effective to clean the medical device.
[26.] The method of embodiment [25], wherein the medical device is a flexible endoscope.
[27.] The method of any one of the above embodiments, wherein cleaning is carried out at a temperature of at least about 20° C.
[28.] The method of any one of the above embodiments, wherein cleaning is carried out for a period of time of at least about 2 minutes of contact time.
[29.] The method of any one of the above embodiments, wherein cleaning is carried out to effectively remove from the medical device at least one of soil, blood, protein, carbohydrate, bodily fluid, and fecal matter.
[30.] The method of any one of the above embodiments, wherein cleaning is carried out for at least two cycles.
[31.] The method of any one of the above embodiments, wherein cleaning is carried out employing a flexible endoscope washer disinfector device.
[32.] The method of any one of the above embodiments, wherein cleaning is carried out employing a flexible endoscope washer disinfector device, wherein multiple flexible endoscopes are washed at the same time.
[33.] The method of any one of the above embodiments, wherein the cleaning includes one or more cycle times, each less than about 25 minutes.
[34.] The method of any one of the above embodiments, further including, after cleaning the medical device, disinfecting the medical device.

[35.] The method of any one of the above embodiments, further including, after cleaning the medical device, disinfecting the medical device and then drying the medical device.

[36.] The method of any one of the above embodiments, wherein the cleaning and optionally the disinfecting and optionally the drying is carried out employing a flexible endoscope washer disinfector device.

[37.] The method of any one of the above embodiments, further including, after cleaning the medical device, after disinfecting the medical device and after drying the medical device, storing the medical device in a sterile environment.

[38.] The method of any one of the above embodiments, wherein any one or more of the cleaning, disinfecting, drying, and storing is carried out employing a WASSENBURG® PAA Cleaner; WASSENBURG® WD440 Endoscope Washer Disinfector; WASSENBURG® WD440 PT Pass Through Endoscope Washer Disinfector; WASSENBURG® DRY300 Drying and Condition Cabinet; and WASSENBURG® DRY200 Endoscope Drying and Conditioning Cabinet.

[39.] The present invention also provides for a kit that includes:
  (a) an enclosed container that includes a removable closure,
  (b) the composition of any one of the above embodiments, located inside the enclosed container, and
  (c) printed indicia located on the enclosed container.

[40.] The present invention also provides for the kit of the above embodiment, wherein the enclosed container is manufactured from high density polyethylene (HDPE).

[41.] The present invention also provides for the kit of any one of the above embodiments, wherein the enclosed container is opaque.

[42.] The present invention also provides for the kit of any one of the above embodiments, wherein the printed indicia includes instructions to avoid excessive heat, to avoid elevated temperatures, to avoid direct sunlight, or a combination thereof.

[43.] The present invention also provides for the kit of any one of the above embodiments, further including a liquid applicator that includes at least one of a spray bottle, wipe, cloth, sponge, non-woven fabric, and woven fabric.

What is claimed is:

1. A composition consisting of:
   (i) a chelator in the form of ethylenediaminetetraacetic acid (EDTA) present in about 0.5 to about 2.0 wt. % of the composition;
   (ii) a buffer system in the form of potassium phosphate dibasic and sodium hydroxide present in a total amount of more than 10 to about 20 wt. % of the composition;
   (iii) a cleaner in the form of diethyl glycol monoethyl ether present in about 2.5 to about 10 wt. % of the composition;
   (iv) a solubilizer in the form of propylene glycol, present in about 2.5 to about 10 wt. % of the composition; and
   (v) a diluent in the form of water present in about 45 to about 80 wt. % of the composition, the composition having a pH of at least about 9.5.

2. The composition of claim 1, wherein the ethylenediaminetetraacetic acid (EDTA) is present in about 1.0 wt. % of the composition;
   the potassium phosphate dibasic and sodium hydroxide are present in about 14.2 wt. % and 2.16 wt. %, respectively, of the composition;
   the diethyl glycol monoethyl ether are present in about 5.0 wt. % of the composition;
   the solubilizer comprises propylene glycol, present in about 10.0 wt. % of the composition;
   the diluent comprises water, present in about 67.64 wt. % of the composition; and the composition has a pH of about 11.9 to about 12.2.

* * * * *